United States Patent
Pugh et al.

(10) Patent No.: US 9,241,669 B2
(45) Date of Patent: Jan. 26, 2016

(54) NEUROMUSCULAR SENSING FOR VARIABLE-OPTIC ELECTRONIC OPHTHALMIC LENS

(75) Inventors: Randall Braxton Pugh, St. Johns, FL (US); Daniel B. Otts, Fruit Cove, FL (US); James Daniel Riall, St. Johns, FL (US); Adam Toner, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 212 days.

(21) Appl. No.: 13/552,046

(22) Filed: Jul. 18, 2012

(65) Prior Publication Data
US 2014/0022505 A1 Jan. 23, 2014

(51) Int. Cl.
| | |
|---|---|
| *G02C 1/00* | (2006.01) |
| *A61B 5/00* | (2006.01) |
| *G02C 11/00* | (2006.01) |
| *G02C 7/04* | (2006.01) |
| *G02C 7/08* | (2006.01) |
| *A61B 5/0488* | (2006.01) |
| *A61F 2/16* | (2006.01) |

(52) U.S. Cl.
CPC .............. *A61B 5/6821* (2013.01); *A61B 5/0488* (2013.01); *G02C 7/04* (2013.01); *G02C 7/083* (2013.01); *G02C 11/10* (2013.01); *A61B 5/04888* (2013.01); *A61F 2/1624* (2013.01)

(58) Field of Classification Search
CPC .................................. G02C 7/04; G02C 11/10
USPC .................. 351/158, 159.02, 159.03
See application file for complete search history.

(56) References Cited

U.S. PATENT DOCUMENTS

| | | | |
|---|---|---|---|
| 2006/0122530 A1 | 6/2006 | Goodall | |
| 2007/0260307 A1 | 11/2007 | Azar | |
| 2008/0208335 A1 | 8/2008 | Blum | |
| 2010/0331977 A1 | 12/2010 | Schaper, Jr. | |
| 2012/0077548 A1 | 3/2012 | Goldberg | |
| 2013/0035760 A1* | 2/2013 | Portney ...................... 623/6.13 |
| 2013/0194540 A1* | 8/2013 | Pugh et al. ............... 351/159.03 |

FOREIGN PATENT DOCUMENTS

| | | |
|---|---|---|
| WO | WO2008091859 A1 | 7/2008 |
| WO | WO 2012/006691 A1 | 1/2012 |
| WO | WO2012006691 A1 | 1/2012 |

OTHER PUBLICATIONS

Search Report issued by the Hungarian Intellectual Property Office completed May 5, 2014 for Singapore Patent Application No. 201305264-2.
Report from the Russian Patent Office for corresponding Application No. 2013131643/28 dated Jan. 16, 2015.
European Search Report for corresponding EPA No. 13177098.4 dated Jul. 11, 2013.

(Continued)

*Primary Examiner* — Huy K Mai (57) ABSTRACT

A variable-optic powered or electronic ophthalmic lens may be utilized to augment the eye's natural ability to refract light or focus. The variable-optic powered lens comprises an electronic system that includes a power source, power management circuitry, clock generation circuitry, control algorithms and circuitry and lens driver circuitry. The ophthalmic lens may also comprise one or more sensors configured to detect ciliary muscle signals and adjust the optics of the lens accordingly.

12 Claims, 2 Drawing Sheets

(56) References Cited

OTHER PUBLICATIONS

Ronald H. Silverman, Ph.D., *High Resolution Ultrasound Imaging of the Eye—A Review*, Clinical and Experimental Ophthalmology, 2009; 37: 54-67.

European Search Report dated Oct. 30, 2013 for corresponding EPA No. 13177098.

* cited by examiner

NEUROMUSCULAR SENSING FOR VARIABLE-OPTIC ELECTRONIC OPHTHALMIC LENS

BACKGROUND OF THE INVENTION

1. Field of the Invention

The present invention relates to a variable-optic powered or electronic ophthalmic lens having a sensor and associated hardware and software for detecting ciliary muscle signals, and more particularly, to a sensor and associated hardware and software for detecting ciliary muscle signals in an individual to activate and control a variable-optic powered or electronic ophthalmic lens.

2. Discussion of the Related Art

As electronic devices continue to be miniaturized, it is becoming increasingly more likely to create wearable or embeddable microelectronic devices for a variety of uses. Such uses may include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neurostimulators. A new, particularly useful field of application is in ophthalmic wearable lenses and contact lenses. For example, a wearable lens may incorporate a lens assembly having an electronically adjustable focus to augment or enhance performance of the eye. In another example, either with or without adjustable focus, a wearable contact lens may incorporate electronic sensors to detect concentrations of particular chemicals in the precorneal (tear) film. The use of embedded electronics in a lens assembly introduces a potential requirement for communication with the electronics, for a method of powering and/or re-energizing the electronics, for interconnecting the electronics, for internal and external sensing and/or monitoring, and for control of the electronics and the overall function of the lens.

The human eye has the ability to discern millions of colors, the ability to adjust easily to shifting light conditions, and transmit signals or information to the brain at a rate exceeding that of a high-speed internet connection. Lenses, such as contact lenses and intraocular lenses, currently are utilized to correct vision defects such as myopia (nearsightedness), hyperopia (farsightedness), presbyopia and astigmatism. However, properly designed lenses incorporating additional components may be utilized to enhance vision as well as to correct vision defects.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered contract lenses may be designed to provide enhanced vision via zoom-in and zoom-out capabilities, or just simply modifying the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low-light conditions. The properly designed electronics and/or arrangement of electronics on lenses may allow for projecting an image onto the retina, for example, without a variable-focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This, coupled with a wireless data transmitter, could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The proper combination of devices could yield potentially unlimited functionality; however, there are a number of difficulties associated with the incorporation of extra components on a piece of optical-grade polymer. In general, it is difficult to manufacture such components directly on the lens for a number of reasons, as well as mounting and interconnecting planar devices on a non-planar surface. It is also difficult to manufacture to scale. The components to be placed on or in the lens need to be miniaturized and integrated onto just 1.5 square centimeters of a transparent polymer while protecting the components from the liquid environment on the eye. It is also difficult to make a contact lens comfortable and safe for the wearer with the added thickness of additional components.

Given the area and volume constraints of an ophthalmic device such as a contact lens, and the environment in which it is to be utilized, the physical realization of the device must overcome a number of problems, including mounting and interconnecting a number of electronic components on a non-planar surface, the bulk of which comprises optic plastic. Accordingly, there exists a need for providing a mechanically and electrically robust electronic contact lens.

As these are powered lenses, energy or more particularly current consumption, to run the electronics is a concern given battery technology on the scale for an ophthalmic lens. In addition to normal current consumption, powered devices or systems of this nature generally require standby current reserves, precise voltage control and switching capabilities to ensure operation over a potentially wide range of operating parameters, and burst consumption, for example, up to eighteen (18) hours on a single charge, after potentially remaining idle for years. Accordingly, there exists a need for a system that is optimized for low-cost, long-term reliable service, safety and size while providing the required power.

In addition, because of the complexity of the functionality associated with a powered lens and the high level of interaction between all of the components comprising a powered lens, there is a need to coordinate and control the overall operation of the electronics and optics comprising a powered ophthalmic lens. Accordingly, there is a need for a system to control the operation of all of the other components that is safe, low-cost, and reliable, has a low rate of power consumption and is scalable for incorporation into an ophthalmic lens.

Each eye contains a ciliary muscle, which is located around or proximate to the crystalline lens. Zonules attach to the ciliary muscle and, additionally, attach to the crystalline lens. The ciliary muscle controls accommodation for viewing objects at varying distances by changing the shape of the crystalline lens. For example, when focusing on a nearby object where a short focal distance is needed, the ciliary muscle contracts and slackens the zonules causing the crystalline lens to become rounder and more compressed. However, when focusing on a distant object and a lengthened focal distance is needed, the ciliary muscle relaxes and the zonules pull on the edges of the crystalline lens causing it to be thinner and flatter. Accordingly, the ciliary muscle and the electrical signals derived therefrom may be utilized as a way to activate and control a powered ophthalmic lens.

Powered or electronic ophthalmic lenses may have to account for the various ciliary muscle signals detected from the individual utilizing the powered or electronic ophthalmic lens. More specifically, powered lenses have to detect and differentiate between various ciliary muscle signals, and from one or more of other signals, noise, and interference. Accordingly, there exists a need for a means and method of detecting ciliary muscle signals and utilizing them to activate an electronic or powered ophthalmic lens according to the type of ciliary muscle signal detected by a sensor, such as contraction or relaxation of the ciliary muscle.

SUMMARY OF THE INVENTION

Neuromuscular sensors in accordance with the present invention overcome the limitations associated with controlling a powered ophthalmic lens based upon feedback signals directly from the wearer.

In accordance with one aspect, the present invention is directed to an electronic ophthalmic lens. The electronic ophthalmic lens comprises a wearable ophthalmic lens having an optic zone and a peripheral zone, a variable-optic element incorporated into the optic zone of the wearable ophthalmic lens, the variable optic being configured to change the refractive power of the wearable ophthalmic lens, and an electronic component incorporated into the peripheral zone of the wearable ophthalmic lens, the electronic component including a sensing system for detecting ciliary muscle movement associated with the process of accommodation, the sensing system configured to generate an action for controlling the variable optic-element.

The present invention relates to a powered contact lens comprising an electronic system which performs any number of functions, including actuating a variable-focus optic. The electronic system includes one or more batteries or other power sources, power management circuitry, one or more sensors, clock generation circuitry, control algorithms and circuitry, and lens driver circuitry.

Control of a powered ophthalmic lens may be accomplished through a manually operated external device that communicates with the lens wirelessly, such as a hand-held remote unit. Alternately, control of the powered ophthalmic lens may be accomplished via feedback or control signals directly from the wearer. For example, sensors built into the lens may sense signals indicative of ciliary muscle movement, i.e., contraction and relaxation. Based upon these signals, the powered ophthalmic lens may change state, for example, its refractive power in order to either focus on a near object or a distant object.

The ciliary muscle is the structure that controls the shape of the crystalline lens. The crystalline lens is encased in an envelope, known as the capsule, which is suspended by fibers, known as zonules, connected to the ciliary muscle. The ciliary muscle causes the zonules to draw tight or to relax thereby changing the shape and focusing power of the crystalline lens to refract incoming or incident light. The iris, or colored part of the eye, is the partition between the anterior and posterior chambers of the eye and it is made up of two muscles that regulate the size of the pupil to control the amount of light entering the eye. The dilator muscle opens the pupil and the sphincter muscle closes the pupil. The eye also has six extraoccular muscles that control the overall movement of the eye or eye globe. The sensing of the extraoccular muscles and/or the dilator and sphincter muscles may provide other or additional functionality for a powered or electronic ophthalmic lens. In the present invention; however, the circuitry is preferably designed to amplify ciliary muscle signals while filtering out interference, noise and other muscle signals.

A sensor, the components of which may be embedded in a contact lens, may detect characteristics of different eye muscle signals. For example, various signals may include one or more of when an eye is moving up or down, focusing up close, and/or adjusting to a change in ambient light levels, such as from light to dark, dark to light and all light conditions in between. The ciliary muscle only controls the shape of the crystalline lens in order to focus the eye on a near or distant object, i.e., accommodation. The sensor in accordance with the present invention relies on tracking various signals, including amplitude, time-domain response and frequency, produced by or emitted from the ciliary muscle in certain sample conditions, such as when an individual is reading, focusing far away, or in a room with fluorescent lighting. These ciliary muscle signal samples may be logged and tracked wherein the various waveforms and frequencies of each of the signals may be distinguished from one or more of other signals, noise, and interference. As set forth above, the circuitry of the present invention is preferably designed to detect, isolate and/or filter and amplify ciliary muscle signals. Whenever the sensor detects a recognized ciliary muscle signal, it may trigger activity in the electronic circuitry, for example, changing the refractive power of the lens. In alternate embodiments, other muscle signals may be utilized for augmenting or implementing other eye functions that the eye can no longer achieve on its own. In addition, the sensor may comprise any suitable means for sensing ciliary muscle action as is explained in detail herein.

The sensor and associated circuitry of the present invention is preferably able to differentiate various ciliary muscle signals from each other and is preferably able to distinguish ciliary muscle signals from other signals, noise, and interference. The sensor and associated circuitry of the present invention provides a convenient, safe, low cost, and reliable means and method for detecting ciliary muscle signals via a variable-optic electronic contact lens, which also has a low rate of power consumption and is scalable for incorporation into an ophthalmic lens.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered contact lenses may be designed to provide enhanced vision via zoom-in and zoom-out capabilities, or just simply modifying the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low light conditions. The properly designed electronics and/or arrangement of electronics on lenses may allow for projecting an image onto the retina, for example, without a variable focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This coupled with a wireless data transmitter could allow a physician to have almost immediate access to a patient's blood chemistry without the need for the patient to waste time getting to a laboratory and having blood drawn. In addition, sensors built into the lenses may be utilized to detect signals from the ciliary muscle of an eye for use in determining what kind of action or movement the eye is trying to perform and activating the electronic lens.

The powered or electronic contact lens of the present invention comprises the necessary elements to correct and/or enhance the vision of patients with one or more of the above described vision defects or otherwise perform a useful ophthalmic function. In addition, they may be utilized simply to enhance normal vision or provide a wide variety of functionality as described above. The electronic contact lens may comprise a variable focus optic lens, an assembled front optic embedded into a contact lens or just simply embedding electronics without a lens for any suitable functionality. The electronic lens of the present invention may be incorporated into any number of contact lenses as described above. However, for ease of explanation, the disclosure will focus on an electronic contact lens to correct vision defects intended for single-use daily disposability.

The present invention is directed to a powered ophthalmic lens or powered contact lens comprising an electronic system, which actuates a variable-focus optic or any other device or devices configured to implement any number of numerous functions that may be performed. The electronic system includes one or more batteries or other power sources, power management circuitry, communication circuitry, one or more sensors, clock generation circuitry, control algorithms and circuitry, and lens driver circuitry. The complexity of these components may vary depending on the required or desired functionality of the lens.

Control of an electronic or a powered ophthalmic lens may be accomplished through a manually operated external device that communicates with the lens, such as a hand-held remote unit. For example, a fob may wirelessly communicate with the powered lens based upon manual input from the wearer. Alternately, control of the powered ophthalmic lens may be accomplished via feedback or control signals directly from the wearer. For example, sensors built into the lens may sense signals indicative of ciliary muscle movement, i.e. contraction and relaxation, to compensate for crystalline lens dysfunction or any other problems associated with visual acuity or eye disease. Based upon these signals, the powered ophthalmic lens may change state, for example, its refractive power, in order to either focus on a near object or a distant object. The ciliary muscle in the eye is the structure that controls or attempts to control the shape of the crystalline lens. The crystalline lens is encased in the capsule which is suspended by zonules connected to the ciliary muscle. The ciliary muscle causes the zonules to contract or to relax thereby changing the shape and/or focusing power of the crystalline lens. If the crystalline is unable to partially or fully respond to ciliary muscle movement, the individual will be unable to accommodate, a disease state known as presbyopia. Therefore, a powered or electronic ophthalmic lens that responds to these same signals may be utilized to compensate for this loss of ability to accommodate.

The iris, or colored part of the eye, is the partition between the anterior and posterior chambers of the eye and it is made up of two muscles that regulate the size of the pupil to control the amount of light entering the eye. The dilator muscle opens the pupil and the sphincter muscle closes the pupil. The eye also has six extraoccular muscles that control the overall movement of the eye or eye globe. The sensing of the extraoccular muscles and/or the dilator and sphincter muscles may provide other or additional functionality for a powered or electronic ophthalmic lens. The eye comprises a number of liquid components, including the tear film. These liquids are excellent conductors of electrical signals as well as other signals, such as acoustic signals or sound waves. Accordingly, it should be understood that a neuromuscular sensor in accordance with the present invention may provide feedback signals for controlling any number of functions that may be implemented by a powered or electronic ophthalmic lens. However, in accordance with the present invention, the circuitry is configured to detect, isolate and amplify ciliary muscle signals while filtering out noise and other muscle signals.

A sensor, the components of which may be embedded in a powered contact lens, may detect characteristics of different eye muscle signals. For example, various signals may include one or more of when an eye is moving up or down, focusing up close, and adjusting to a change in ambient light levels, such as from light to dark, dark to light or any other light condition. The ciliary muscle only controls the shape of the crystalline lens in order to focus on a near or distant object. The sensor relies on tracking various signals, including amplitude, time-domain response and frequency composition, produced by or emitted from the ciliary muscle in certain sample conditions, such as when an individual is reading, focusing far away, or in a room with fluorescent lighting. It is important to note that this list of conditions is exemplary and not exhaustive. These ciliary muscle signal samples may be logged and tracked wherein the various waveforms and frequencies of each of the signals may be distinguished from one or more of other signals, noise, and interference. As set forth above, the circuitry of the present invention is preferably designed to detect, isolate and/or filter ciliary muscle signals. In alternate embodiments, other muscle signals may be utilized for augmenting or implementing other ocular functions. Whenever the sensor detects a recognized ciliary muscle signal, it may trigger activity in the electronic circuitry, for example, activating an electronic lens.

As set forth herein, the crystalline lens of the eye is suspended by zonules, the fibers that are attached to both the crystalline lens and the ciliary muscle. The ciliary muscle reacts to various stimuli and sends out any number of signals that are normally interpreted by the central nervous system whereupon some action takes place. For example, in accommodation, when the retina receives an image from a close or near object, the ciliary muscle contracts. This contraction causes the zonules to relax and allows the crystalline lens to thicken which in turn makes the lens stronger (adding plus power) which is needed to focus on a close up or near object. This process is known as accommodation. More specifically, this is one of the more widely accepted theories of how the ciliary muscle works in conjunction with the zonules and the crystalline lens in accommodation. In individuals with presbyopia, the crystalline lens becomes less flexible, and thus may not move regardless of the ciliary muscle contraction. Even though the crystalline lens does not respond, the ciliary muscle still contracts or otherwise reacts and sends out a measurable signal and this measurable signal may be utilized with a powered lens to compensate for the lack of response by the crystalline lens. In other words, regardless of the theory of how the precise mechanism of accommodation works relative to the ciliary muscle, the ciliary muscle does react to different stimuli and thus its response may be measured with the right sensors. Accordingly, a complete set of ciliary muscle responses may be measured under various conditions or stimuli and a set of data developed to be utilized as a set of feedback signals for controlling a powered or electronic ophthalmic lens directly. The powered or electronic ophthalmic lens may be utilized to compensate for various visual acuity problems, including presbyopia, as well as any number of other conditions.

There may be various methods used to implement some exemplary embodiments of the present invention. For example, a sensor may detect a ciliary muscle signal utilizing one or more of electromyography (EMG), magnetomyography (MMG), phonomyography (PMG), and impedance. Furthermore, a sensor may comprise a non-contact sensor, such as an antenna that is embedded into a contact lens, but that does not directly touch the surface of an eye. Alternately, a sensor may comprise a contact sensor, such as contact pads that directly touch the surface of an eye. It is important to note that any number of suitable devices and processes may be utilized for the detection of signals from the ciliary muscle as is explained in detail subsequently.

As described herein, any type of sensor and/or sensing technology may be utilized. In accordance with an alternate exemplary embodiment, ultrasound biomicroscopy may be utilized to image the ciliary body region of the eye. With ultrasound biomicroscopy, it is possible to distinguish and analyze the changes in the ciliary muscle contour in different accommodation states. Since changes in ciliary muscle contour may be detected in this manner, the results or changes may be provided to and utilized in accordance with the present invention in the same manner as any other sensing device.

Figure 1:
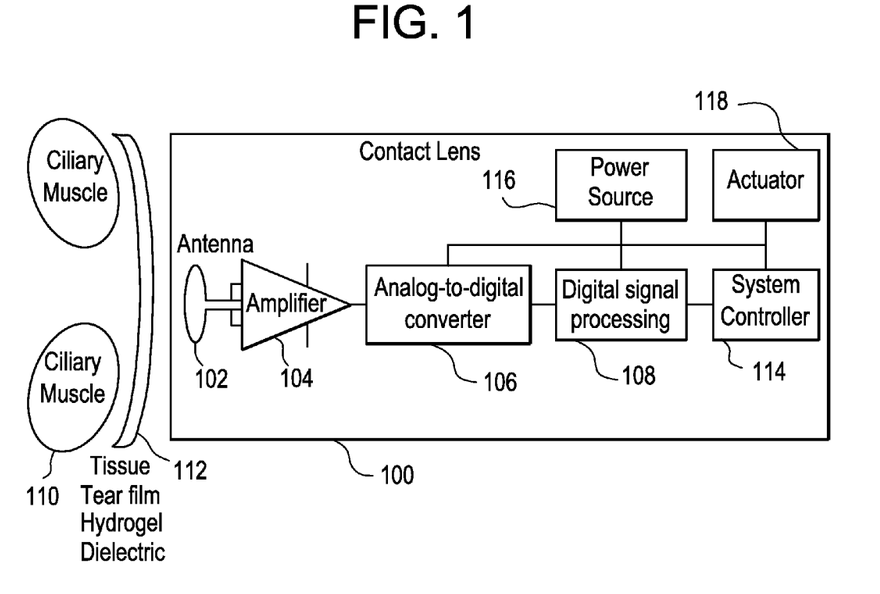
FIG. 1 illustrates an exemplary contact lens comprising a non-contact sensor in accordance with some embodiments of the present invention.

FIG. 1 illustrates, in block diagram form, a contact lens 100, comprising a non-contact sensor system, shown on the front surface of the eye or cornea 112, in accordance with one exemplary embodiment of the present invention. In this exemplary embodiment, the non-contact sensor system may comprise an antenna 102, an amplifier 104, an analog-to-digital converter 106, a digital signal processor 108, a power source 116, an actuator 118, and a system controller 114. As illustrated, the ciliary muscle 110 is located behind the front eye surface or cornea 112. More specifically, the globe of the eye can be divided into two segments; namely, the anterior chamber and the posterior chamber. The iris is the partition between the anterior and posterior chambers. Between the front surface of the crystalline lens and the back surface of the iris is the posterior chamber. At the base of the iris is the ciliary body which produces aqueous humor and is continuous with the ciliary muscle. The contact lens 100 is placed onto the front surface of the eye 112 wherein the electronic circuitry of the sensor system may be utilized to implement the neuromuscular sensing of the present invention. The antenna 102 as well as the other circuitry is configured to sense signals from ciliary muscle 110 actions through the various tissue and liquids forming the eye and produced by the eye. As set forth above, the various fluids comprising the eye are good conductors of electrical and acoustical signals.

In this exemplary embodiment, the antenna 102 may be embedded into the contact lens 100 and isolated from the eye and tear film on the front surface of the eye 112 by a dielectric. A non-contact antenna 102 may operate as a receptor to detect an electromagnetic signal produced by the ciliary muscle 110 of the eye. For example, there may be various signals detected by an antenna 102 depending on the state that a ciliary muscle is in, such as whether it is contracting or relaxing, or on the type of action that a ciliary muscle is trying to perform, such as causing the eye to focus on a near object or a far object. The antenna 102 may comprise any suitable device for capturing the signals from the ciliary muscle 110. In one exemplary embodiment, the antenna 102 may comprise a single loop antenna. The amplifier 104 may amplify a signal to a useable level for the remainder of the system, such as giving a signal enough power to be acquired by the analog-to-digital converter 106. In addition to providing gain, the amplifier 104 may include other analog signal conditioning circuitry such as filtering and impedance matching circuitry appropriate to the antenna 102 and amplifier 104 output. The amplifier 104 may comprise any suitable device for amplifying and conditioning the signal output by the antenna 102. For example, the amplifier 104 may simply comprise a single operational amplifier or a more complicated circuit comprising one or more operational amplifiers. As set forth above, the antenna 102 and the amplifier 104 are configured to capture and isolate the signals from the ciliary muscle from the noise and other signals produced in or by the eye and convert it to a signal usable ultimately by the system controller 114. The system controller 114 is preferably preprogrammed to recognize the various signals produced by the ciliary muscle under various conditions and provide an appropriate output signal to the actuator 118.

In this exemplary embodiment, the analog-to-digital converter 106 may be used to convert an analog signal output from the amplifier into a digital signal for processing. For example, the analog-to-digital converter 106 may convert an analog signal output from the amplifier 104 into a digital signal that may be useable by subsequent or downstream circuits, such as a digital signal processing system 108 or microprocessor. A digital signal processing system or digital signal processor 108 may be utilized for digital signal processing, including one or more of filtering, processing, detecting, and otherwise manipulating/processing sampled data to discern a ciliary muscle signal from noise and interference. The digital signal processor 108 may be preprogrammed with the ciliary muscle responses described above. The digital signal processor 108 may be implemented utilizing analog circuitry, digital circuitry, software and/or preferably a combination thereof. For example, various ciliary muscle signals that may occur within a certain frequency range may be distinguishable from other signals, noise, and interference that occur within other frequency ranges. Certain commonly occurring noise and interference signals may be notched at various stages in the signal acquisition chain utilizing analog or digital filters, for example, harmonics of 50/60 Hz AC mains and fluorescent lights.

A power source 116 supplies power for numerous components comprising the non-contact sensor system. The power may be supplied from a battery, energy harvester, or other suitable means as is known to one of ordinary skill in the art. Essentially, any type of power source may be utilized to provide reliable power for all other components of the system. A ciliary muscle signal, processed from analog to digital, may enable activation of the system controller 114. Furthermore, the system controller 114 may control other aspects of a powered contact lens depending on input from the digital signal processor 108, for example, changing the focus or refractive power of an electronically controlled lens through an actuator 118.

In further alternate exemplary embodiments, the system controller 114 may receive input from sources including one or more of a contact sensor, a blink detector, and a fob control. By way of generalization, it may be obvious to one skilled in the art that the method of activating and/or controlling the system controller 114 may require the use of one or more activation methods. For example, an electronic or powered contact lens may be programmable specific to an individual user, such as programming a lens to recognize both of an individual's ciliary muscle signals when performing various actions, for example, focusing on an object far away, or focusing on an object that is near, and an individual's blink patterns. In some exemplary embodiments, using more than one method to activate an electronic contact lens, such as ciliary muscle signal detection and blink detection, may give the ability for each method to crosscheck with another before activation of the contact lens occurs. An advantage of crosschecking may include mitigation of false positives, such as minimizing the chance of unintentionally triggering a lens to activate. In one exemplary embodiment, the crosschecking may involve a voting scheme, wherein a certain number of conditions are met prior to any action taking place.

The actuator 118 may comprise any suitable device for implementing a specific action based upon a received command signal. The actuator 118 may comprise an electrical device, a mechanical device, a magnetic device or any combination thereof. The actuator 118 receives a signal from the system controller 114 in addition to power from the power source 116 and produces some action based on the signal from the system controller 114. For example, if the system controller 114 signal is indicative of the wearer trying to focus on a near object, the actuator 118 may be utilized to somehow change the refractive power of the electronic ophthalmic lens.

Figure 2:
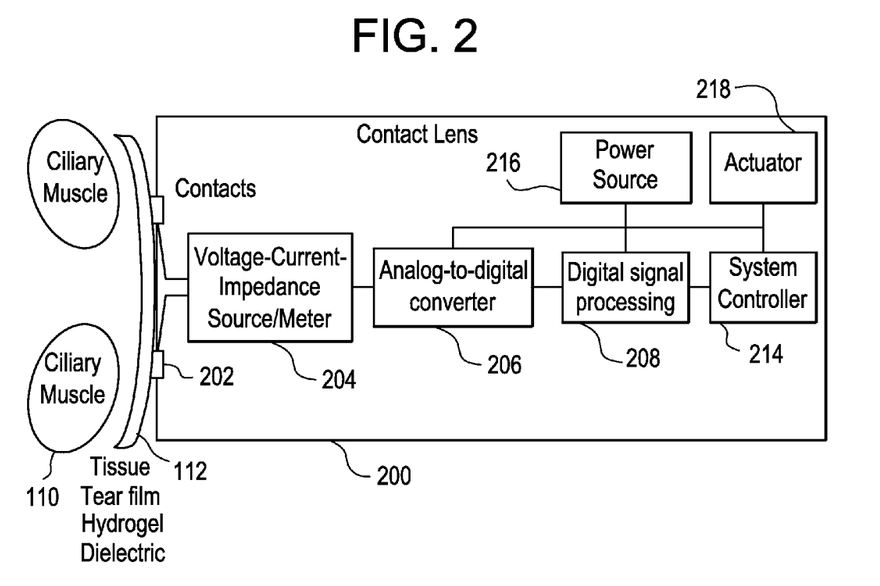
FIG. 2 illustrates an exemplary contact lens comprising a contact sensor in accordance with some embodiments of the present invention.

FIG. 2 illustrates a contact lens 200, comprising a contact sensor system, shown on the front surface of the eye or cornea 112 in accordance with another exemplary embodiment of the present invention. In this exemplary embodiment, a contact sensor system may comprise a contact or multiple contacts 202, a voltage-current-impedance source/meter 204, an analog-to-digital converter 206, a digital signal processor 208, a power source 216, an actuator 218, and a system controller 214. The ciliary muscle 110 is located behind the front eye surface or cornea 112. The contact lens 200 is placed onto the front surface of the eye 112, such that the electronic circuitry of the sensor may be utilized to implement the neuromuscular sensing of the present invention. The components of this exemplary system are similar to and perform the same functions as those illustrated in FIG. 1, with the exception of contacts 202 and the source/meter 204. In other words, since direct contacts 202 are utilized, there is no need for an antenna or an amplifier to amplify and condition the signal received by the antenna.

In the illustrated exemplary embodiment, the contacts 202 may provide for a direct electrical connection to the tear film and the eye surface. For example, the contacts 202 may be implemented as metal contacts that are exposed on the back curve of the contact lens 200 and be made of biocompatible conductive materials, such as gold or titanium. Furthermore, the contact lens polymer may be molded around the contacts 202, which may aid in comfort on the eye and provide improved conductivity through the contact lens 200. Additionally, the contacts 202 may provide for a low resistance connection between the eye's surface 112 and the electronic circuitry within the contact lens 200. Four-terminal sensing, also known as Kelvin sensing, may be utilized to mitigate contact resistance effects on the eye. The source/meter 204 may emit a signal with several constituent frequencies or a frequency sweep, while measuring the voltage/current across the contacts 202.

In an alternate exemplary embodiment, a source/meter 204 may be configured to read a potential difference across the eye arising from a voltage or current produced by the contraction or relaxation of the ciliary muscle 110. It is important to note that various types of sensors may be utilized, given that the eye comprises various fluids, including tears which are excellent conductors.

The source/meter 204 may be configured to measure the impedance of an eye wherein the impedance may change in a certain location based upon what a ciliary muscle is trying to do, such as contracting or relaxing. In this exemplary embodiment, the analog-to-digital converter 206 and the digital signal processing 208 may be configured differently for a contact-based sensor as opposed to a non-contact based sensor, as described in FIG. 1. For example, there may be a different sample rate, a different resolution, and different signal processing algorithm 208.

Figure 3:
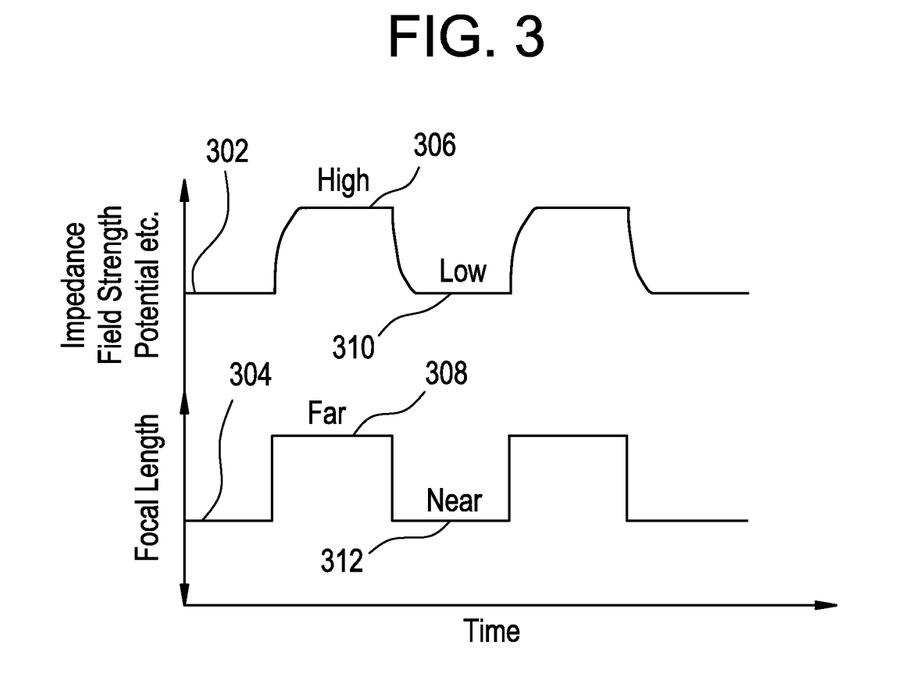
FIG. 3 is a graphical representation demonstrating correlations between measurable electrical parameters and the eye's desired focal length in accordance with the present invention.

FIG. 3 illustrates a graph demonstrating correlations between measurable electrical parameters and the eye's focal length as described in the referenced literature. Trace 302 is a representation of an electrically measurable signal in or on the eye. For example, such signals may be detected as one or more of impedance, voltage potential, induced electromagnetic field, and other measurable parameters. Trace 304 is a representation of a desired focal length wherein for example, if clinical subjects focused on objects at 0.2 and 2.0 meter distances, the ciliary muscle may undergo a corresponding change in measurable electrical parameters accordingly, depending on the distance of focus. However, using the same example, the actual focal length of a lens may not change or only changes minimally, such as in cases where a person may be presbyopic and the lens of the eye is too rigid and unable to accommodate for a change in focus, even where the ciliary muscles are responding to the change. As described in the literature, there is a correlation between a measurable electrical signal and a focal length. As illustrated in FIG. 3, impedance is high 306 when the focal length is far 308 and impedance is low 310 when the focal length is near 312. Additionally, as described in the literature but not illustrated in FIG. 3, a correlation exists between the amplitude of traces 302 and 304 for intermediate values.

In some exemplary embodiments, characteristics of an electrical signal 302 such as shape, frequency content, timing, and amplitude, may vary due to several factors including one or more of a detection method utilized (e.g., impedance or field strength), an individual's eye physiology, ciliary muscle fatigue, electrolyte levels in the eye, state of presbyopia, interference, and focal length. For example, depending on the type of detection method used, the correlation between desired focus and measurable electrical parameter may have the opposite polarity from what is illustrated in FIG. 3. Additionally, for example, an electrical signal may be distorted from carrying one or more of significant noise, interference from other muscles, and interference from various environmental sources or due to the effects of aging, disease or genetics. Accordingly, studies of eye response and individual user measurement and training may be used to program the digital signal circuitry to properly detect the eye's desired focal length. Parameters of the digital signal processing may be adjusted in response to other measurements, for example, time of day, measured electrolyte levels, ambient light levels and the like. Furthermore, recorded samples of a user's eye focus signals may be used in conjunction with interference detection and mitigation techniques.

It is important to note that any type of sensor may be utilized in accordance with the present invention. As long as there is muscle movement associated with changing conditions, it may be sensed, processed and utilized to enhance, augment or simply provide vision correction.

Figure 4:
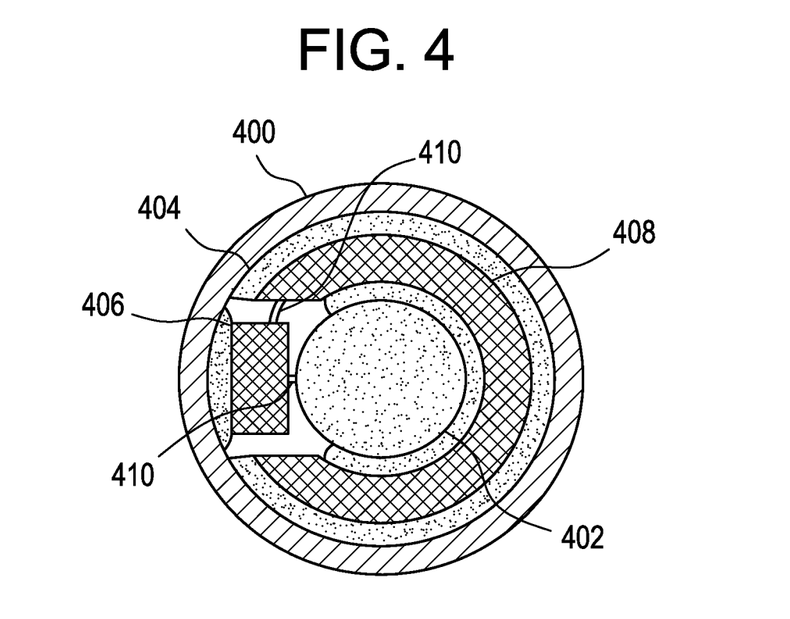
FIG. 4 is a planar view of an ophthalmic lens comprising electronic components, including a sensor circuit, and a variable-optic element in accordance with the present invention.

Referring now to FIG. 4, there is illustrated, in planar view, a wearable electronic ophthalmic lens comprising a neuromuscular sensor in accordance with the present invention. The ophthalmic lens 400 comprises an optic zone 402 and a peripheral zone 404. The optic zone 402 may function to provide one or more of vision correction, vision enhancement, other vision-related functionality, mechanical support, or even a void to permit clear vision. In accordance with the present invention, the optic zone 402 may comprise a variable optic element configured to provide enhanced vision at near and distant ranges based on signals sensed from the ciliary muscle. The variable-optic element may comprise any suitable device for changing the focal length of the lens or the refractive power of the lens based upon activation signals from the sensing system described herein. For example, the variable optic element may be as simple as a piece of optical grade plastic incorporated into the lens with the ability to have its spherical curvature changed. The peripheral zone 404 comprises one or more of electrical circuits 406, a power source 408, electrical interconnects 410, mechanical support, as well as other functional elements. The electronic circuits 406 may comprise one or more integrated circuit die, printed electronic circuits, electrical interconnects, and/or any other suitable devices, including the sensing circuitry described herein. The power source 408 may comprise one or more of battery, energy harvesting, and or any other suitable energy storage or generation devices. It is readily apparent to the skilled artisan that FIG. 4 only represents one exemplary embodiment of an electronic ophthalmic lens and other geometrical arrangements beyond those illustrated may be utilized to optimize area, volume, functionality, runtime, shelf life as well as other design parameters. It is important to note that with any type of variable optic, the fail safe is distance vision. For example, if power were to be lost or if the electronics fail, the wearer is left with an optic that allows for distance vision.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An electronic ophthalmic lens comprising:
   a wearable ophthalmic lens having an optic zone and a peripheral zone;
   a variable optic element incorporated into the optic zone of the wearable ophthalmic lens, the variable optic being configured to change the refractive power of the wearable ophthalmic lens; and
   an electronic component incorporated into the peripheral zone of the wearable ophthalmic lens, the electronic component including a sensing system for detecting ciliary muscle movement, contraction and relaxation, associated with the process of accommodation, the sensing system including a wireless sensor, an amplifier, and circuitry for detecting, isolating and filtering ciliary muscle signals including a power source, a signal processor, a controller and an actuator and configured to generate an action for controlling the variable-optic element, the wireless sensor comprising an antenna configured to detect electromagnetic signals produced by the ciliary muscle, the electromagnetic signals including amplitude, time-domain response and frequency composition of ciliary muscle output.

2. The electronic ophthalmic lens according to claim 1, wherein the wearable ophthalmic lens comprises a contact lens.

3. The electronic ophthalmic lens according to claim 2, wherein the contact lens comprises a soft contact lens.

4. The electronic ophthalmic lens according to claim 1, wherein the power source comprises a battery.

5. The electronic ophthalmic lens according to claim 4, wherein the signal processor comprises a digital signal processor.

6. The electronic ophthalmic lens according to claim 5, wherein the controller comprises a microprocessor.

7. The electronic ophthalmic lens according to claim 6, wherein the actuator is operatively associated with the variable-optic element.

8. An electronic ophthalmic lens comprising:
   a wearable ophthalmic lens having an optic zone and a peripheral zone;
   a variable optic element incorporated into the optic zone of the wearable ophthalmic lens, the variable optic being configured to change the refractive power of the wearable ophthalmic lens; and
   an electronic component incorporated into the peripheral zone of the wearable ophthalmic lens, the electronic component including a sensing system for detecting ciliary muscle movement, contraction and relaxation, associated with the process of accommodation, the sensing system including a contact based sensor and circuitry for detecting, isolating and filtering ciliary muscle signals including a voltaqe-current impedence source/meter, an analog-to-digital converter, a power source, a signal processor, a controller and an actuator and configured to generate an action for controlling the variable optic element, wherein the contact based sensor comprises one or more contacts configured to make direct electrical contact with the tear film of the eye to detect electrical signals produced by the ciliary muscle, including amplitude, time-domain response and frequency composition.

9. The electronic ophthalmic lens according to claim 8, wherein the power source comprises a battery.

10. The electronic ophthalmic lens according to claim 9, wherein the signal processor comprises a digital signal processor.

11. The electronic ophthalmic lens according to claim 10, wherein the controller comprises a microprocessor.

12. The electronic ophthalmic lens according to claim 11, wherein the actuator is operatively associated with the variable-optic element.

* * * * *